United States Patent [19]

Ionescu et al.

[11] Patent Number: 4,629,459
[45] Date of Patent: Dec. 16, 1986

[54] ALTERNATE STENT COVERING FOR TISSUE VALVES

[75] Inventors: Marian I. Ionescu, Leeds, England; Jay A. Lenker, Laguna Beach; Philip S. Yang, Irvine, both of Calif.

[73] Assignee: Shiley Inc., Irvine, Calif.

[21] Appl. No.: 566,133

[22] Filed: Dec. 28, 1983

[51] Int. Cl.⁴ .............................................. A61F 2/24
[52] U.S. Cl. .......................................... 623/2; 623/900
[58] Field of Search ............................. 3/1.5, 1; 623/2

[56] References Cited

U.S. PATENT DOCUMENTS

| | | | |
|---|---|---|---|
| 3,276,448 | 10/1966 | Kronenthal | 3/1 X |
| 3,667,472 | 6/1972 | Halpern | 3/1 X |
| 3,714,671 | 2/1973 | Edwards et al. | 3/1 |
| 3,983,581 | 10/1976 | Angell et al. | 3/1.5 |
| 4,079,468 | 3/1978 | Liotta et al. | 3/1.5 |
| 4,084,268 | 4/1978 | Ionescu et al. | 3/1.5 |
| 4,172,295 | 10/1979 | Batten | 3/1.5 |
| 4,364,126 | 12/1982 | Rosen et al. | 3/1.5 |
| 4,441,216 | 4/1984 | Ionescu et al. | 3/1.5 |
| 4,491,986 | 1/1985 | Gabbay | 3/1.5 |

OTHER PUBLICATIONS

Bartek et al., "Frame-Mounted Tissue Heart Valves: Technique of Construction"; Thorax, vol. 29, pp. 51-55 (1974).

Primary Examiner—Richard J. Apley
Assistant Examiner—Alan W. Cannon
Attorney, Agent, or Firm—Charles J. Knuth; Lawrence C. Akers; Mark Dryer

[57] ABSTRACT

A prosthetic heart valve comprising a stent having an annular base and a plurality of legs extending upwardly from said base; a valve element circumscribing said stent and attached thereto, said valving element comprising a number of cooperating valve leaflets equal to the number of said legs; and a layer of biologically-compatible material secured to said stent and positioned between said stent and said leaflets, said layer having a smooth, non-abrasive outer surface and covering all of the surfaces of said stent that, in the absence of said layer, would contact the mobile portions of said leaflets during the normal function of the valve.

24 Claims, 8 Drawing Figures

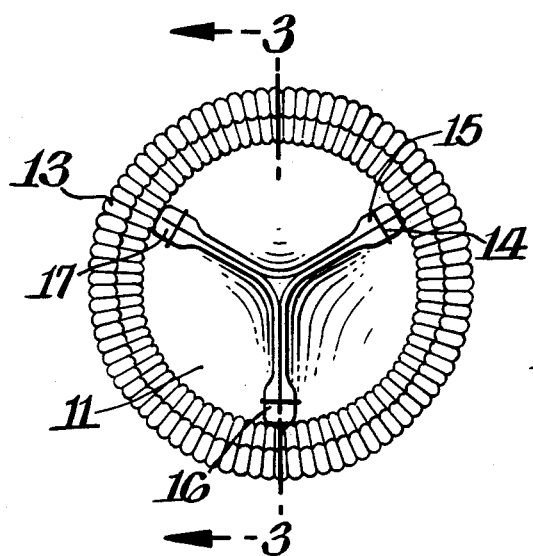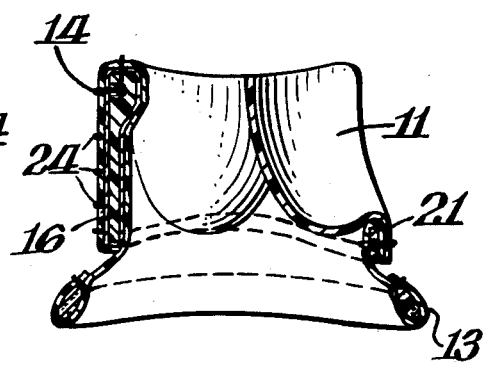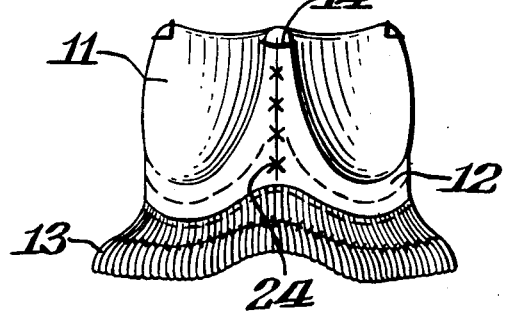

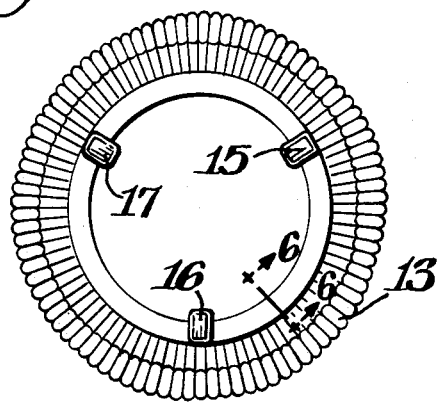
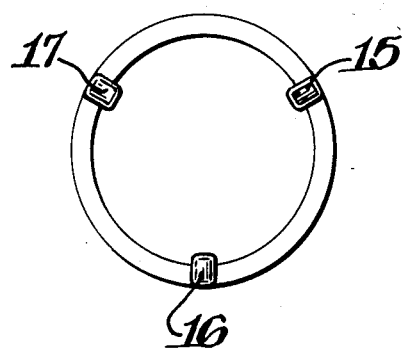
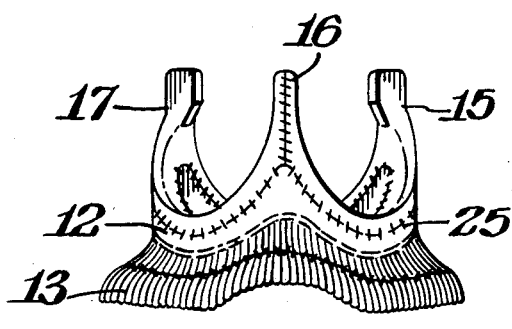
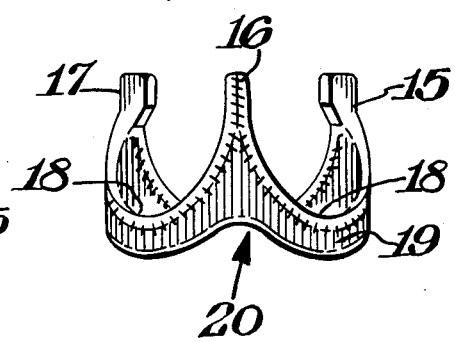
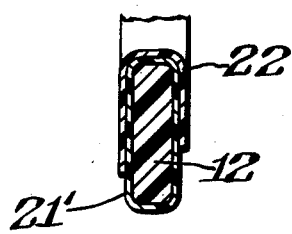

ALTERNATE STENT COVERING FOR TISSUE VALVES

BACKGROUND OF THE INVENTION

This invention relates to an improved prosthetic heart valve with a padded stent. More particularly, the invention is concerned with a prosthetic heart valve comprising a stent having a smooth, non-abrasive outer layer adapted to avoid abrasion damage during normal function of the valve.

The early development of prosthetic heart valves is well documented in papers given at symposia in 1960 and in 1968, published in PROSTHETIC HEART VALVES, Lyman A. Brewer, III, Ed., Charles C. Thomas Publishing Co., Springfield, Ill. (1969), Second National Conference on Prosthetic Heart valves; PROSTHETIC VALVES FOR CARDIAC SURGERY, K. Alvin Merendino, Editor, Thomas Publishing Co., Springfield, Ill. (1961).

Lefrak and Starr recently surveyed the development of cardiac valve prostheses, E. A. Lefrak, and A. Starr, CARDIAC VALVE PROSTHESES, Appleton-Century-Krofts, New York, 1979 and the development of tissue heart valves has been comprehensively reviewed by Ionescu, Marian I., TISSUE HEART VALVES, Butterworths, Boston, 1979.

Great efforts have been expended in the development of tissue heart valve prostheses and in the development of supportive structures, or stents, for tissue valves. Representative of efforts to develop stents for tissue valves are the disclosures in the following U.S. Pat. Nos. 3,570,014, W. D. Hancock, Mar. 16, 1971; 3,714,671, William Sterling Edwards, et al, Feb. 6, 1973; 3,755,823, W. D. Hancock, Sept. 4, 1973: 3,983,581, William W. Angell, Oct. 5, 1976; 4,035,849, William W. Angell et al, July 19, 1977; 4,079,468, Domingo Santo Liotta, Mar. 21, 1978: 4,084,268, Marian I. Ionescu et al, Apr. 18, 1978; 4,106,129, Alain F. Carpentier, et al, Aug. 15, 1978; 4,172,295, Richard J. Batten, Oct. 30, 1979 and 4,192,020, Richard B. Davis, et al, Mar. 11, 1980. Other structures are also reported in the aforementioned treatises on heart valve developments.

Some of the earliest heart valve prostheses were flexible two-or three-cusp valves in which the cusps were constructed of various types of fabric. Some of these flexible leaflet valves had good flow characteristics but most failed early. The leaflets tore, separated from the annulus, or became rigid due to fibrous tissue ingrowth. From about 1960 into the 1970's, the trend was to mechanical valves. These ranged from the mechanically quite simple Starr-Edwards valve to the relatively sophisticated Bjork-Shiley valve and included a number of disc poppet valves. These mechanical valves generally dominated the market and are still very satisfactory for many applications. Tissue valves are still the preferred treatment where anti-coagulation therapy is not tolerated by the patient.

In 1962, Donald Ross and Sir Brian Barratt-Boyes, independently, were performing implantations of homograft tissue valves some of which were free graft implants and some were mounted on supporting stents. Fully clothed covered rigid stents were used in some of these homograft valves.

In 1965, Drs. Binet and Carpentier, and their associates, implanted a specially prepared porcine aortic valve xenograft. These porcine valves were sterilized and treated, e.g. with formaldehyde, and were commonly attached to a metal stent. Experience showed that these valves were of short life, largely because formaldehyde was used as the cross-linking agent. Formaldehyde was found to create reversible cross links in the tissue, thereby allowing early breakdown of the tissue. Dr. Carpentier, in about 1968, established the concept of the bioprosthesis by substantially eliminating antigenicity of the tissue, principally by changing the preservative from formaldehyde to glutaraldehyde. Glutaraldehyde has been shown to create cross links of a more permanent nature than those created by formaldehyde.

A number of porcine bioprostheses and specially designed stents for supporting these prostheses resulted from the efforts of Warren Hancock et al. Generally, pig aortic valves are procured under clean conditions placed in a cold, balanced electrolyte solution, excess tissue is trimmed and the xenografts are immersed in 0.2% glutaraldehyde. The leaflets are held in their normal valving postion under pressure during the tanning process and each valve is sutured to a cloth covered stent by multiple sutures. A number of designs and stent constructions for the Hancock type valve are exemplified in the aforementioned U.S. Pat. Nos. 3,570,014 and 3,755,823. Stents for porcine valves were developed by a number of other workers also, see, e.g., U.S. Pat. Nos. 3,983,581; 4,035,849; 4,079,468 and 4,106,129.

Stents for supporting cusp valves of other tissue members, e.g. fascia lata and pericardium, have been developed by a number of workers, see, e.g., U.S. Pat. No. 3,714,671. Much of the pioneering work in this area of valve development was done by Dr. Marian I. Ionescu and his associates, see, e.g., Bartek, et al, FRAME-MOUNTED TISSUE HEART VALVES: TECHNIQUE OF CONSTRUCTION, Thorax, Volume 29, Pages 51–55, 1974; Ionescu, et al, HEART VALVE REPLACEMENT WITH IONESCU-SHILEY PERICARDIAL XENOGRAFT, Cardiology Digest, June, 1977; Ionescu, et al, HEART VALVE REPLACEMENT WITH IONESCU-SHILEY PERICARDICAL XENOGRAFT, The Journal of Thoracic and Cardiovascular Surgery, Volume 73, Pages 31–42, 1977; Tandon, et al, LONG-TERM HEMODYNAMIC EVALUATION OF AORTIC PERICARDIAL XENOGRAFT, British Heart Journal, Volume 40, Pages 602–607, 1978; Ionescu, et al, LONG-TERM CLINICAL AND HEMODYNAMIC EVALUATION OF THE IONESCU-SHILEY PERICARDIAL XENOGRAFT HEART VALVE, Thoraxchirurgie, volume 25, Pages 250–258, 1978; Ionescu, et al, LONG-TERM SEQUENTIAL HEMODYNAMIC EVALUATION OF RIGHT VENTRICULAR OUTFLOW TRACT RECONSTRUCTION USING A VALVE MECHANISM, The Annals of Thoracic Surgery, 27, 425–434, 1979; and Ionescu, Editor, TISSUE HEART VALVES, Butterworths, 1979.

A number of improvements in the basic Ionescu tissue heart valve have been made. For example, a tissue heart valve has been developed which has a cloth-covered stent of special construction, in which the outflow annulus diameter of the valve is defined and limited by the positioning of a coaptation stitch on the inside of the supporting legs of the stent, as has been the practice since the early development of the Ionescu type tissue heart valve. Another improvement in the method for aligning the tissue of the cusps of the Ionescu type heart valve is described in U.S. Pat. No. 4,172,295 which also disclosed the coaptation stitch inside the stent legs.

A heart valve with a removable cusp protector band is disclosed in U.S. Pat. No. 4,364,126.

A potential problem remains in the heart valves described in the above references, namely, that stress is concentrated in the tissue in some areas where sharp bending of the tissue around the stent occurs. The stress tends to be highest at points of maximum curvature such as around the tips of the stent legs because of the pinching of the tissue leaflets together inside and above the tip of the stent leg. A solution to this problem is disclosed in U.S. patent application Ser. No. 327,081, filed Dec. 3, 1981. U.S. Pat. No. 4,441,216, issued Apr. 10, 1984).

A further problem of prior art prosthetic heart valves is the abrasion caused by the rubbing of a tissue valve leaflet over a fabric covered stent. This problem is substantially solved by the present invention.

SUMMARY OF THE INVENTION

In accordance with the present invention there is provided a prosthetic heart valve comprising;

a stent having an annular base and a plurality of legs extending upwardly from said base:

a valving element circumscribing said stent and attached thereto, said valving element comprising a number of cooperating valve leaflets equal to the number of said legs; and for the purpose of avoiding abrasion damage caused by the rubing of said leaflets over said stent, a layer of biologically compatible material secured to said stent and positioned between said stent and said leaflets, said layer having a smooth, non-abrasive outer surface and covering all of the surfaces of said stent that, in the absence of said layer, would contact the mobile portions of said leaflets during the normal function of the valve.

Said smooth, non-abrasive layer of biologically compatible material provides an effective padding over and above any prior art fabric covering on the stent and the presence of such padding substantially extends the durability of the valve as demonstrated hereinafter. The term "smooth" as used herein is intended to mean at least that degree of smoothness which substantially overcomes the abrasion problem experienced in a valve having a stent covered with the relatively "rough" fabric covering disclosed in the prior art reference.

The layer of biologically compatible material is preferably a sheet of a synthetic polymeric material, for example, polyurethane, a silicone elastomer or polytetrafluoroethylene: or a sheet of natural tissue, for example pericardial tissue. The pericardial tissue preferably is cross-linked and the cross-linking may be achieved by fixation or tanning of the tissue, for example, with glutaraldehyde, before or after its attachment to the stent.

Alternatively the layer may be a coating of the said synthetic polymeric material or a coating of organic material, for example collagen or gelatin. Such coating may be applied by dipping the stent into a solution or other liquid form of the coating material.

The invention also provides a stent for use in a prosthetic heart valve, as described above, which comprises an annular base, a plurality of legs extending upwardly from said base and a layer of biologically-compatible material secured to and covering all the surfaces of the stent, the said layer having a smooth, non-abrasive outer surface, the said outer surface being that which contacts the mobile portions of the leaflets in the heart valve for which the stent is adapted to be used.

The material used for the stent according to the invention may be any of the known conventional materials, for example, titanium, Delrin (an acetal homopolymer), polyacetal, polypropylene or Elgiloy (an alloy of cobalt, chromium and nickel).

It is preferred that the biologically-compatible material used to form the layer covering the surfaces of the stent has a greater compliance than the material from which the stent is made.

Compliance, as applied to a prosthetic material may be defined as a mechanical matching characteristic depending upon the elastic response of the material when subjected to pressure and stresses comparable to those experienced by the natural material present at the site of the prosthesis. The term is described, for example, in U.S. Pat. No. 4,173,689.

In another preferred embodiment of the invention the prosthetic heart valve additionally comprises a layer of fabric covering the entire surface of and attached to the stent, and positioned between the stent and the layer of biologically-compatible material.

As in the previously described embodiments the biologically-compatible material is preferably a synthetic polymeric material, for example, polyurethane, a silicone elastomer or polytetrafluoroethylene; or a natural tissue material, for example pericardial tissue, which may be cross-linked. The biologically-compatible material may be attached to the fabric by means of a biologically-compatible glue or by means of sutures. When sutures are used they are located so that no abrasion results.

The layer of biologically-active material may be a coating of polymeric material, preferably a silicone elastomer or polyurethane, applied to the layer of fabric.

In a further embodiment of the invention the layer of biologically-compatible material is a coating of an organic material, for example collagen or gelatin, which may be cross-linked or uncross-linked.

BRIEF DESCRIPTION OF DRAWINGS

The invention will now be more particularly described with reference to the accompanying drawings, in which:

FIG. 1 is a side elevation of a prosthetic heart valve having a pericardial padding on a covered stent;

FIG. 2 is a top plan view of the valve of FIG. 1:

FIG. 3 is a sectional view taken along section line 3—3 in FIG. 2;

FIG. 4 is a perspective view of a padded covered stent with a cloth sewing ring:

FIG. 5 is a plan view of the stent-sewing ring assembly of FIG. 4:

FIG. 6 is a sectional view taken along section line 6—6 in FIG. 5:

FIG. 7 is a perspective view of a padded, covered stent without sewing ring: and FIG. 8 is a plan view of the stent of FIG. 7.

DETAILED DESCRIPTION OF PREFERRED EMBODIMENTS

Referring to the embodiments of the invention illustrated in the drawings, FIG. 1 illustrates a prosthetic heart valve comprising a valving element having three tissue leaflets 11, a stent assembly 12 and a suture or sewing ring assembly 13. The coaptation stitches 14 across the top of the stent legs cause coaptation or joining of the edges of the tissue leaflets around the stent legs. Stitches 24 join the edges of the tissue leaflet forming lines or seams on the outside of the valve. Stitches 25 (FIG. 4) hold down the padding to the cloth covering of the stent.

As shown in FIG. 2 the stent assembly has three substantially identical legs 15,16,17. The configuration of the legs is shown in more detail in FIGS. 4 and 7. The legs extend upwardly toward the outflow end of the valve from the lower-most portion of the stent base 19 and each of the legs is separated from its neighboring legs by a scallop 18 as best shown in FIG. 7. The bottom or inflow edge of the stent, indicated by arrow 20 in FIG. 7, is also scalloped to conform generally to the arc of the scallops between the legs. These bottom scallops generally follow the configuration of the scallops 18 of the outflow edge so as to generally form parallel edges defining the annular ring or base 19, which defines the flow orifice of the valve.

The scallops of the lower or inflow edge of the base and the scallops of the outflow edge between the legs vertically define three generally elliptically shaped one-third portions of the base between the centerlines of the respective upright legs which together circumferentially form a right cylinder of constant diameter with the legs extending parallel to the axis of the cylinder.

Referring again to FIGS. 1, 2 and 3, a sewing or suture ring 13 extends outwardly circumferentially forming an annulus vertically following the scalloped curvature of the base 19 (FIG. 7) of the stent. The sewing ring provides a place wherein the surgeon may anchor his sutures when sewing the valve into its position in the heart. This ring may be in any of the forms disclosed in the prior art.

In one embodiment of the invention a layer of material 21 (FIG. 3) covers the stent and is joined along the lower edge of the stent, to which the sewing ring is attached.

In this embodiment of the invention the layer 21 may be a layer of biologically-compatible material having a smooth non-abrasive outer surface as described above.

Alternatively, as illustrated in FIG. 6, the layer of material 21' covering the surface of the stent is a layer of fabric, as described above, and this in turn is covered with a layer 22 of biologically-compatible material having a smooth non-abrasive outer surface.

In a further embodiment the layer of biologically-compatible material may be a coating of a smooth non-abrasive surface material applied to the layer of fabric 21'.

Heart valves provided with a layer of biologically-compatible material having a smooth, non-abrasive outer surface secured to and covering all the surfaces of the stent that are in contact with the leaflets, in accordance with the invention, were subjected to in vitro life cycle testing.

The tests were conducted in a Rowan Ash heart valve fatigue tester using a solution containing 0.2% glutaraldehyde in normal saline solution.

In a typical in vitro experiment, valves that were padded in accordance with the invention lasted an average of $220 \times 10^6$ cycles before failure, whereas unpadded counterparts, made according to standard prior art procedure, failed after an average of $74 \times 10^6$ cycles.

These results show a three fold increase in durability of the valves according to the invention as compared to prior art counterparts.

We claim:
1. A prosthetic heart valve comprising:
a stent having an annular base and a plurality of legs extending upwardly from said base;
a valve element circumscribing said stent and attached thereto, said valving element comprising a number of cooperating valve leaflets equal to the number of said legs; and, for the purpose of avoiding abrasion damage caused by the rubbing of said leaflets over said stent,
a layer of biologically-compatible material secured to said stent and positioned between said stent and said leaflets, said layer having a smooth, non-abrasive outer surface and covering all of the surfaces of said stent that, in the absence of said layer, would contact the mobile portions of said leaflets during the normal function of the valve.

2. A prosthetic heart valve according to claim 1, wherein said layer is a sheet of a smooth surface synthetic polymeric material.

3. A prosthetic heart valve according to claim 2, wherein said synthetic polymeric material is polyurethane, a silicone elastomer or polytetrafluoroethylene.

4. A prosthetic heart valve according to claim 1, wherein said layer is a sheet of natural tissue.

5. A prosthetic heart valve according to claim 4, wherein said natural tissue is pericardial tissue.

6. A prosthetic heart valve according to claim 5, wherein the pericardial tissue is cross-linked.

7. A prosthetic heart valve according to claim 6, wherein the cross-linking of the pericardial tissue is achieved by fixation of the tissue before or after its attachment to the stent.

8. A prosthetic heart valve according to claim 1, wherein said layer is a smooth coating of synthetic polymeric material.

9. A prosthetic heart valve according to claim 8, wherein the synthetic polymeric material is polyurethane or a silicone elastomer.

10. A prosthetic heart valve according to claim 1 comprising additionally a layer of fabric covering the entire surface of and attached to said stent, and positioned between said stent and said layer of biologically-compatible material.

11. A prosthesis according to claim 10, wherein said layer of biologically-compatible material is a sheet of a smooth surface synthetic polymeric material.

12. A prosthesis according to claim 11, wherein said synthetic polymeric material is polyurethane, a silicone elastomer or polytetrafluoroethylene.

13. A prosthes is according to claim 10, wherein said layer of biologically-compatible material is a sheet of natural tissue.

14. A prosthesis according to claim 13, wherein said natural tissue is pericardial tissue.

15. A prosthesis according to claim 14, wherein the pericardial tissue is cross-linked.

16. A prosthesis according to claim 15, wherein the cross-linking is achieved by fixation of the tissue before or after its attachment to the fabric covered stent.

17. A prosthesis according to claim 10, wherein said layer of biologically-compatible material is a smooth coating of polymeric material applied to said layer of fabric.

18. A prosthesis according to claim 17, wherein said polymeric material is a silicone elastomer or polyurethane.

19. A prosthesis according to claim 10 wherein the biologically-compatible material is attached to the fabric by means of a biologically-compatible glue.

20. A prosthesis according to claim 10 wherein the biologically-compatible material is attached to the fabric by means of sutures.

21. A prosthesis according to claim 10, wherein said layer of biologically-compatible material is a coating of organic material applied to the fabric.

22. A prosthesis according to claim 21, wherein the organic material is cross-linked collagen, uncross-linked collagen, cross-linked gelatin or uncross-linked gelatin.

23. A prosthesis according to claim 1, wherein the biologically-compatible material has a greater compliance than the material from which the stent is made.

24. A stent for use in a prosthetic heart valve, which comprises an annular base, a plurality of legs extending upwardly from said base and a layer of biologically-compatible material secured to and covering all the surfaces thereof, the said layer having a smooth, non-abrasive outer surface, the said outer-surface being that which contacts the mobile portions of the leaflets in the heart valve for which the stent is adapted to be used.

* * * * *